United States Patent
Helevirta et al.

(10) Patent No.: US 10,010,351 B2
(45) Date of Patent: Jul. 3, 2018

(54) IMPLANT, IMPLANTATION TOOL, KIT AND METHOD

(75) Inventors: Pertti Helevirta, Pirkkala (FI); Harri Happonen, Tampere (FI); Timo Pohjonen, Tampere (FI); Arvi Kruusing, Oulu (FI)

(73) Assignee: Inion Oy (FI)

( * ) Notice: Subject to any disclaimer, the term of this patent is extended or adjusted under 35 U.S.C. 154(b) by 810 days.

(21) Appl. No.: 12/394,828

(22) Filed: Feb. 27, 2009

(65) Prior Publication Data

US 2010/0217266 A1    Aug. 26, 2010

(30) Foreign Application Priority Data

Feb. 23, 2009   (EP) ..................................... 09100138

(51) Int. Cl.
    *A61B 17/56*      (2006.01)
    *A61B 17/68*      (2006.01)
    (Continued)

(52) U.S. Cl.
    CPC ........ *A61B 17/683* (2013.01); *A61B 17/0401* (2013.01); *A61B 17/864* (2013.01); *A61B 17/866* (2013.01); *A61B 17/8863* (2013.01); *A61F 2/0811* (2013.01); *A61B 17/80* (2013.01); *A61B 17/846* (2013.01);
    (Continued)

(58) Field of Classification Search
CPC ..... A61B 17/58; A61B 17/86; A61B 17/0401; A61B 17/683; A61B 17/80; A61B 17/846; A61B 17/864; A61B 17/866; A61B 17/8863; A61B 17/00004; A61B 17/0408; A61B 17/0409; A61B 17/0422; A61F 2002/0835; A61F 2002/0852; A61F 2002/0864; A61F 2002/0888; A61F 2002/30065; A61F 2210/0071; A61C 8/00
USPC ......... 606/76, 300, 329, 264, 265, 301, 315, 606/217, 72, 74, 59, 331; 424/422, 423
See application file for complete search history.

(56) References Cited

U.S. PATENT DOCUMENTS 3,981,307 A * 9/1976 Borysko ........................ 606/227
5,403,348 A * 4/1995 Bonutti ........................ 606/232
(Continued)

FOREIGN PATENT DOCUMENTS

GB       2084468 A    4/1982
WO      99/52478 A1   10/1999
(Continued)

OTHER PUBLICATIONS

Immergut et al., Principles of Plasticization, Advance in Chemistry; American Chemical Society: Washington, DC, Pub. Jan. 1, 1965, http://pubs.acs.org.*

(Continued)

*Primary Examiner* — Cris L Rodriguez
*Assistant Examiner* — Mirayda A Aponte
(74) *Attorney, Agent, or Firm* — Banner & Witcoff, Ltd.

(57) ABSTRACT

An implant to be fastened to a tissue, a tool a kit and a method. The implant has a first end, a second end and an elongated shank made in part from a first polymer material. The implant includes a contact surface for receiving external mechanical energy for deforming the shape of the implant such that the shape of the implant can be deformed and locked in the tissue by the effect of the external mechanical energy.

15 Claims, 9 Drawing Sheets

(51) Int. Cl.
*A61B 17/04* (2006.01)
*A61B 17/86* (2006.01)
*A61B 17/88* (2006.01)
*A61F 2/08* (2006.01)
*A61C 8/00* (2006.01)
*A61B 17/80* (2006.01)
*A61B 17/84* (2006.01)
*A61B 17/00* (2006.01)
*A61F 2/30* (2006.01)

(52) U.S. Cl.
CPC ............ *A61B 2017/00004* (2013.01); *A61B 2017/0408* (2013.01); *A61B 2017/0409* (2013.01); *A61B 2017/0422* (2013.01); *A61C 8/005* (2013.01); *A61C 8/0054* (2013.01); *A61F 2002/0835* (2013.01); *A61F 2002/0852* (2013.01); *A61F 2002/0864* (2013.01); *A61F 2002/0888* (2013.01); *A61F 2002/30065* (2013.01); *A61F 2210/0071* (2013.01)

(56) References Cited

U.S. PATENT DOCUMENTS

| | | | |
|---|---|---|---|
| 5,413,606 A * | 5/1995 | Fisk et al. | 128/898 |
| 5,968,047 A * | 10/1999 | Reed | 606/76 |
| 6,059,817 A * | 5/2000 | Bonutti | A61B 17/0401 |
| | | | 606/216 |
| 6,080,161 A | 6/2000 | Eaves, III et al. | |
| 6,281,262 B1 | 8/2001 | Shikinami | |
| 6,296,641 B2 * | 10/2001 | Burkhead et al. | 623/13.14 |
| 6,503,278 B1 | 1/2003 | Pohjonen et al. | |
| 2001/0004693 A1 | 6/2001 | Burkhead et al. | |
| 2003/0125744 A1 | 7/2003 | Contiliano et al. | |
| 2004/0053196 A1 * | 3/2004 | Mayer | A61B 17/68 |
| | | | 433/173 |
| 2005/0182411 A1 | 8/2005 | DeMeo et al. | |
| 2007/0260250 A1 | 11/2007 | Wisnewski et al. | |
| 2007/0270833 A1 * | 11/2007 | Bonutti et al. | 606/61 |
| 2008/0021465 A1 | 1/2008 | Shadduck et al. | |
| 2008/0109080 A1 | 5/2008 | Aeschlimann et al. | |
| 2008/0262517 A1 * | 10/2008 | Wieland | A61B 17/00491 |
| | | | 606/151 |

FOREIGN PATENT DOCUMENTS

| | | | |
|---|---|---|---|
| WO | WO 9952478 A1 * | 10/1999 | ......... A61B 17/0401 |
| WO | 02/069817 A1 | 12/2002 | |
| WO | 03/028535 A2 | 4/2003 | |
| WO | 2004014857 A1 | 2/2004 | |
| WO | 2008/034277 A2 | 3/2008 | |
| WO | 2008/116203 A2 | 9/2008 | |
| WO | 2008112912 A2 | 9/2008 | |
| WO | 2008125849 A1 | 10/2008 | |
| WO | 2008130954 A2 | 10/2008 | |

OTHER PUBLICATIONS

English abstract of WO 02/069817.
Extended European Search Report relating to corresponding EP Application No. 09100138.8.
Office Action issued for corresponding Taiwanese Patent Application No. 99103756, dated Oct. 15, 2014.
Search Report issued for corresponding Taiwanese Patent Application No. 99103756, dated Oct. 15, 2014.
Medizintechnik Opposition issued in European U.S. Pat. No. 2221014 corresponding to U.S. Appl. No. 12/394,828.
Woodwelding Opposition issued in European patent No. 2221014 corresponding to U.S. Appl. No. 12/394,828.
Schwarz et al., Kunststoffverabeitung,vol. 8, pp. 81, 108, 109, 1999.
Tadmor et al., Molecular Orientation in Injection Modling, Journal of Applied Polymer Science, vol. 18, pp. 1753-1772, 1974.

* cited by examiner

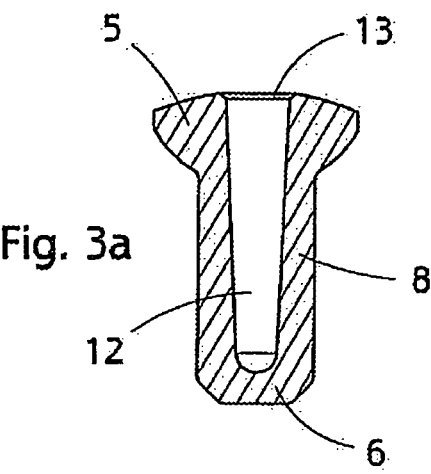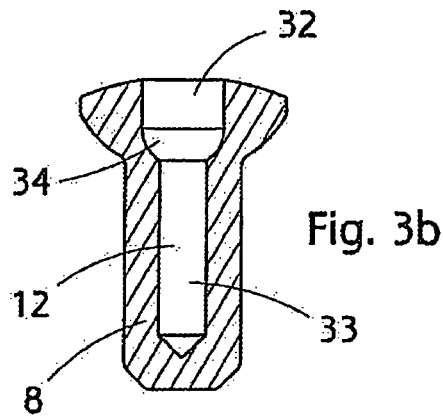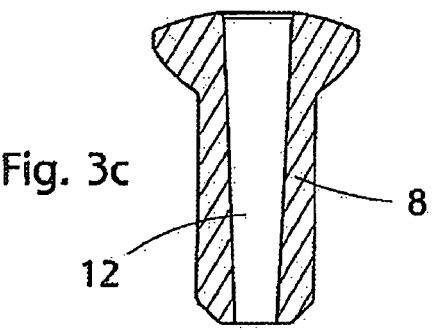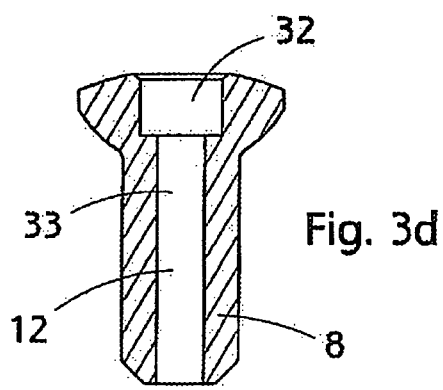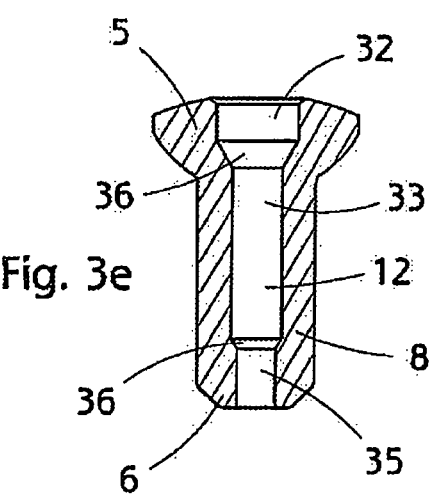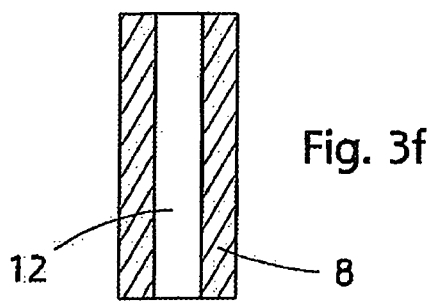

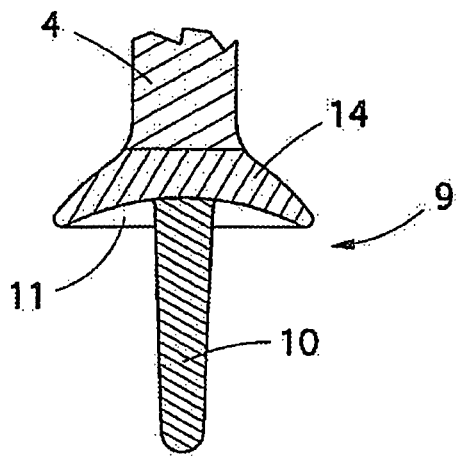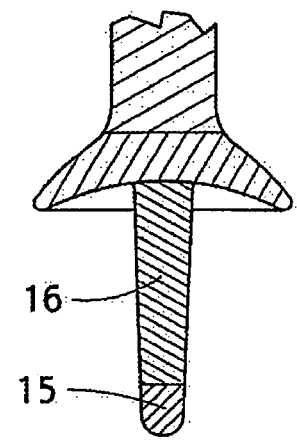
Fig. 4a Fig. 4b
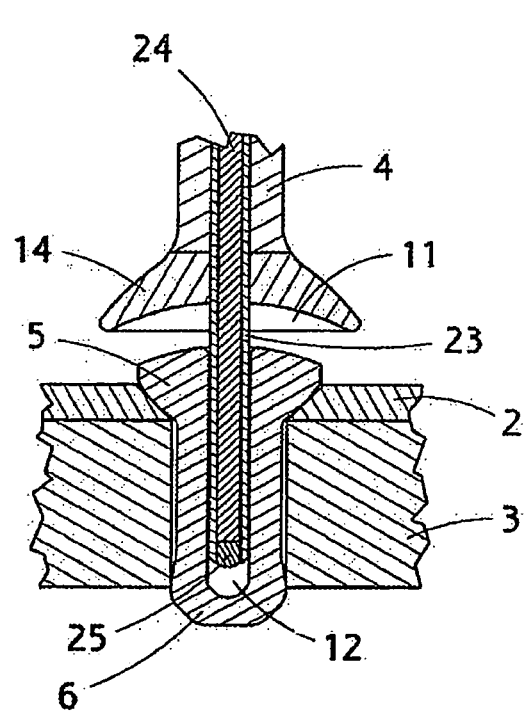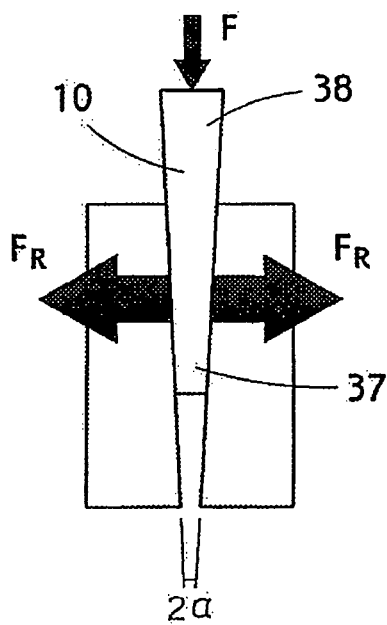
Fig. 8 Fig. 9

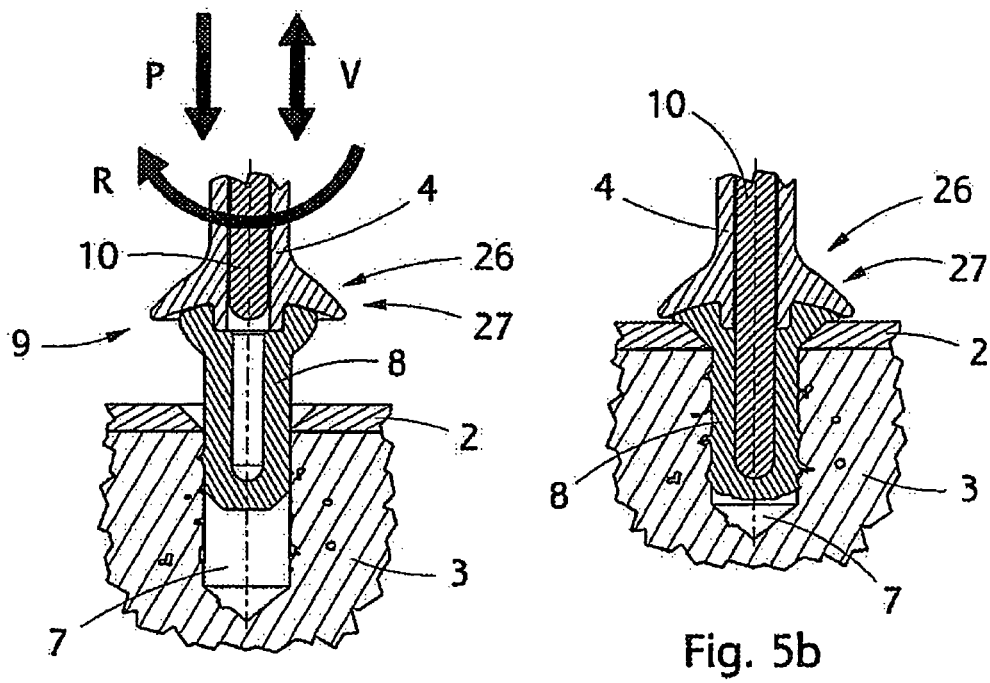
Fig. 5a
Fig. 5b
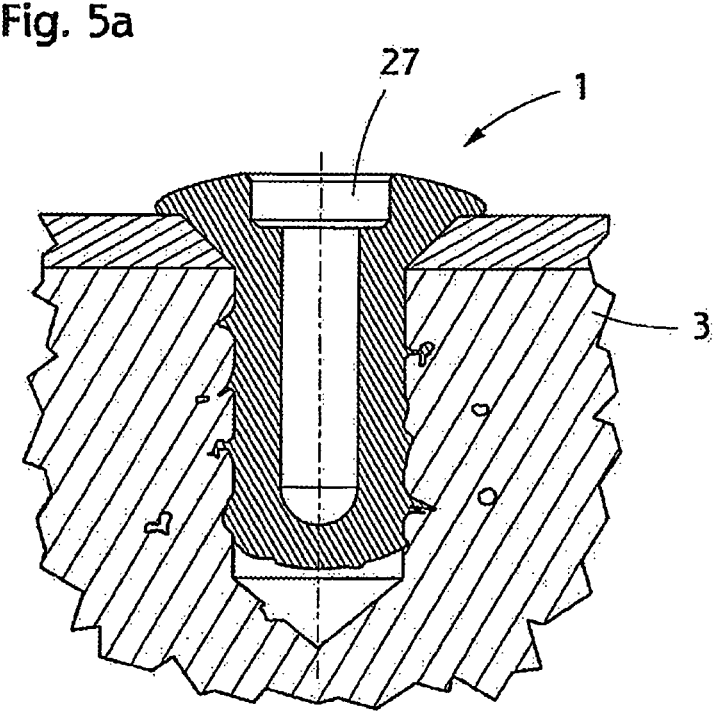
Fig. 5c

IMPLANT, IMPLANTATION TOOL, KIT AND METHOD

RELATED APPLICATION

This application claims priority from European patent application number 09100138.8, filed Feb. 23, 2009 which is hereby incorporated herein by reference in its entirety for all purposes.

FIELD

The present invention relates to an implant to be fastened to a tissue, the implant having a first end, a second end and an elongated shank made at least partly of a first polymer material.

The present invention further relates to an implantation tool for fastening an implant to a tissue, the implant being made at least partly of a first polymer material, the tool comprising a body and shaping means arranged at said body.

The present invention further relates to a kit for fastening a material to a tissue.

The present invention further relates to a method for fastening a material to a tissue.

BACKGROUND

In the prior art, screws and pins, for example, are used for fastening implants to a tissue. A problem with screws is, however, that the fastening is slow. A problem with pins is, in some cases, an insufficient pull-out strength.

To avoid these problems, other fastening solutions have also been developed. EP1363543 describes a fastening means, which is arranged in a tissue, after which its outer surface is melted by mechanical energy. As the fastening means is simultaneously pressed against the tissue, molten surface material of the fastening means pours into the tissue pores and provides a positive locking with the tissue. A problem with this solution is that the temperature of the tissue around the fastening means may rise so high that the tissue will be damaged. U.S. Pat. No. 6,080,161 describes a fastener, which is heated as a whole to at least the transition temperature or as high as the melting temperature of the manufacturing material of the fastener. Problems here include the above mentioned heating of tissues and a relatively weak pull-out strength.

BRIEF DESCRIPTION

An object of the present invention is thus to provide an implant, a tool and a kit so as to overcome the above problems. The objects of the invention are achieved by an implant, a tool and a kit which are characterized by what is stated in the independent claims. The preferred embodiments of the invention are disclosed in the dependent claims.

According to an embodiment of the invention the implant comprises a contact surface for receiving external mechanical energy for deforming the shape of the implant such that the shape of the implant can be deformed and locked in a hole by the effect of said mechanical energy.

According to another embodiment of the invention the implantation tool comprises a shaping element, said shaping element being configured to deform the shape of the implant mechanically.

According to still another embodiment of the invention the kit for fastening a material to a tissue comprises one or more implants of claim 1 and at least one implantation tool of claim 11.

According to still another embodiment of the invention the method for fastening a material to a tissue comprises steps of: arranging an implant in a mounting hole in said tissue, the implant having a first end, a second end, an elongated shank made at least partly of a first polymer material, and a contact surface for receiving external mechanical energy for deforming the shape of the implant, directing mechanical energy to the contact surface, and deforming the shape of the implant and locking it in the mounting hole by the effect of said mechanical energy.

The invention is based on the idea of mechanically loading or shaping the implant in order to fasten it to a tissue and that, to permanently shape the implant, the implant or a part thereof need not be melted or the implant need not even be heated to the transition temperature, such as a Tg temperature or an orientation temperature, but the body temperature is sufficient when the implant is shaped mechanically.

An advantage of the implant, tool and kit of the invention is that the implant may be fastened to a tissue very quickly. It is still possible to achieve a firm pull-out strength with the implant. Another advantage is that the temperature at the interface between the implant and the tissue remains low during the entire fastening process, and tissue damages caused by a high temperature can be avoided.

The idea of a preferred embodiment of the invention is that certain parts of the implant, but not the whole implant, are heated to a suitable transition temperature, such as a Tg temperature or an orientation temperature, wherefore the above-mentioned mechanical loading or shaping of the implant may be performed more quickly. In this way, it is possible to fasten the implant even more quickly.

BRIEF DESCRIPTION OF THE DRAWINGS

In the following the invention will be described in greater detail by means of preferred embodiments with reference to the accompanying drawings, in which FIGS. 3a to 3f are schematic elevation views of implants according to the invention, FIGS. 4a and 4b are schematic elevation views of tools according to the invention, FIGS. 5a to 5c are schematic elevation views of a second series of steps in the use of an implant and a tool according to the invention, FIG. 8 is a schematic elevation view of a tool according to the invention, FIG. 9 is a schematic view of an operational principle of a tool and an implant according to the invention.

DETAILED DESCRIPTION OF CERTAIN PREFERRED EMBODIMENTS

For the sake of clarity, the figures show the invention in a simplified manner. Like reference numbers identify like elements.

Figure 1A:
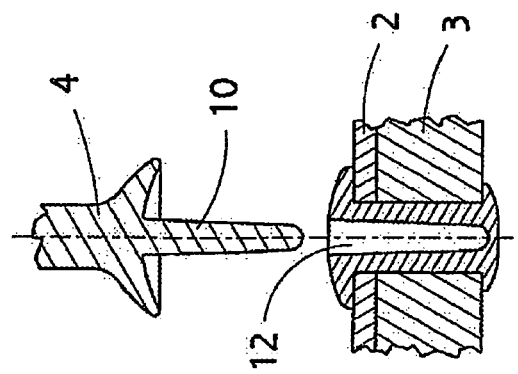
FIGS. 1a to 1c are schematic elevation views of a series of steps in the use of an implant and a tool according to the invention.
Figure 1B:
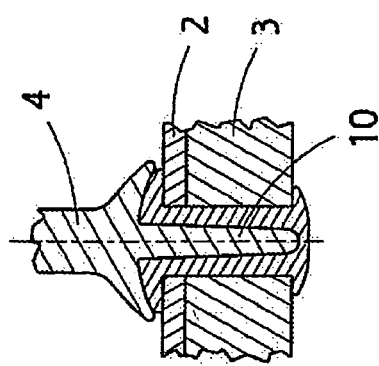
Figure 1C:
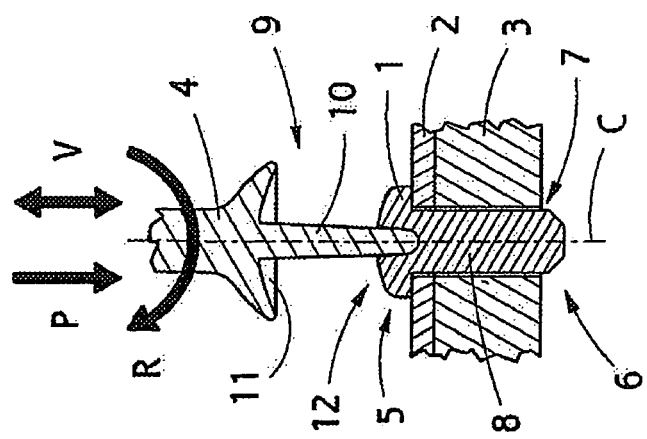

FIGS. 1a to 1c are schematic elevation views of a series of steps in the use of an implant and a tool according to the invention.

In the figures, a plate 2 is fastened to a bony tissue 3 by using an implant 1. The implant 1 comprises a first end 5 provided with a head, the diameter of which is bigger than that of an elongated shank 8 of the implant. The first end 5 also comprises a hole 12 arranged concentrically to the longitudinal central axis C of the implant.

The cross section of the shank 8 is round and the diameter is the same essentially along its entire length.

A second end 6 of the implant is provided with bevel surfaces, which, among other things, facilitate the mounting of the implant in its mounting hole 7.

In FIG. 1a, the implant 1 is arranged through a mounting opening in the plate 2 into the mounting hole 7 provided in the bone 3. The mounting hole 7 is formed in a manner known per se.

The implant 1 is made of a first polymer material, which may be a biodegradable or biostable thermoplastic material.

The first polymer material may be a polymer, copolymer, polymer mixture or polymer composite that dissolves in the organ system. Thus, the first polymer material may be a cyclic ester polymer, copolymer, polymer mixture or polymer composite that can be copolymerized for instance with lactic acid, L-lactide, D-lactide, D,L-lactide, mesolactide, glycolic acid, glycolide or the like and optionally also with some other lactide. The manufacturing material can also comprise other comonomers providing desired properties for the material, such as alpha.-, beta.- and gamma.-hydroxy butyric acid, alpha.-, beta.- and .gamma.-hydroxy valerianic acid and other hydroxy fatty acids (C.sub.11 to C.sub.25), such as stearic acid, palmitinic acid, oleic acid, lauric acid and the like. The manufacturing material can thus be polylactide, polyglycolide, poly(L-lactide), poly(D-lactide), poly(L-lactide-co-D,L-lactide), poly(L-lactide-co-mesolactide), poly(L-lactide-co-glycolide), poly(L-lactide-co-.epsilon.-caprolactone), poly(D, L-lactide-co-mesolactide), poly(D,L-lactide-co-glycolide), poly(D,L-lactide-co-.epsilon.-caprolactone), poly(mesolactide-co-glycolide), poly(mesolactide-co-.epsilon.-caprolactone) or the like. The monomer units of the copolymer basic material can be present in ratios from 50:50 to 85:15 or in some other ratio within this range. Suitable copolymeric manufacturing materials include poly(L-lactide-co-D,L-lactide) 70:30, poly(L-lactide-co-D,L-lactide) 80:20, poly(L-lactide-co-glycolide) 85:15 and poly(L-lactide-co-glycolide) 80:20.

The first polymer material can also contain trimethylene carbonate or dioxanone. Such manufacturing materials include poly(L-lactide-co-trimethylenecarbonate), poly(D,L-lactide-co-trimethyleneca rbonate), poly(mesolactide-co-trimethylenecarbonate), poly(glycol-co-trimethylenecarbonate), poly(L-lactide-co-dioxanone), poly(D,L-lactide-co-dioxanone), poly(mesolactide-co-dioxanone), poly(glycol-co-dioxanone) and the like.

Poly(L-lactide), poly(L-lactide-co-D,L-lactide), poly(L-lactide-co-glycolide), poly(L-lactide-co-trimethylenecarbonate) and their mixtures are especially preferable manufacturing materials of the implant.

In addition to the above-mentioned biodegradable polymers, the first polymer material may be a biostable polymer, copolymer or polymer mixture. It may polyethylene or polyketone, such as PEEK.

It should be noted that the polymers and copolymers suitable for manufacturing materials are known per se and they can easily be prepared by preparation methods known per se to a person skilled in the art.

The implant may also be made of a mixture, one component of which is said first polymer material.

The manufacturing material of the implant 1 is either made at least essentially entirely of the first polymer material or is a mixture comprising both the first polymer material and one or more second polymer materials, filler, functional additive, etc.

The implant 1 may contain various additives and modifiers that improve the processability of the manufacturing material, such as plasticizers and antioxidants, or the material can be dyed with a coloring agent to improve the visibility of the implant and make its handling easier. The components of the implant can also contain one or more bioactive, bone growth stimulating, or pharmaceutically active agents, like antibiotics, growth hormones or anticoagulants. Also, any bioceramic or bioactive glass (e.g., in the form of powder, flakes or fibers), which has been found to enhance bone healing, can be used as an additive. Typical examples of such bioceramics and bioactive glasses useful in this invention: hydroxyapatite, tricalcium phosphate and other calcium phosphates, Bioglass®. (available from Research Center, University of Florida, Gainsville, Fla., USA), Ceravital®, Alumina, Zirconia, Bioactive gel-glass and other bioactive glasses.

The plate 2 is a plate used in surgical procedures and known per se. Thus, it may have a shape of an elongated bar or the letter L, T, X or Y, or it may be rectangular, round or oval, or substantially planar or curved in a predetermined manner, or a plate with some other shape known per se and used for connecting bone parts to one another.

The mounting openings for the plate are arranged as one or more rows. The mounting openings may be formed before the operation or during the operation, for instance in situ just before the implant 1 is arranged.

The diameters of both the mounting opening in the plate 2 and the mounting hole 7 provided in the bone are suitably bigger than the diameter of the shank 8 of the implant. The implant 1 is thus quite easy to mount in its mounting hole 7 in the space shown in FIG. 1a. In the case of FIG. 1a, the implant 1 is mounted by using a tool 4 shown in the figure. The implant 1 may also be mounted in the mounting hole 7 manually or by using instruments known per se. The shank 8 of the implant is so long that it extends through the bone 3 to its other side.

The implant 1, and thus the plate 2, are fastened to the bone by the tool 4, of which only a part is shown. At the part of the tool not shown in the figure is arranged a handle or some other member known per se, with which the tool is used.

At the end of the tool 4 are shaping means 9 comprising heating means and a shaping element. In this case the shaping element comprises, as integral parts of the tool 4 body, a pin 10 and an optional shaping surface 11, on whose symmetry axis the pin 10 is arranged.

Here, the shaping surface 11 is a concave domed surface, but it may also have a convex or a substantially straight shape, etc.

The pin 10 is somewhat conical so that the diameter of its cross section tapers towards the tip. The tip part of the pin 10 may also be rounded, but it may be sharp, too.

The pin 10 and the shaping surface 11 may be heated to such a temperature that part of the implant 1 can be heated with it to a transition temperature of the first polymer material. In this case, the outer sections of the shank 8 may be called the first section and the inner sections the second section. However, it is to be noted that the first section and the second section may be arranged in some other manner with respect to one another, such as one after another in the longitudinal direction of the shank 8. Said first and second section are typically inseparably integrated in each other and made of the same material.

The transition temperature depends on the polymer material and is typically above the body temperature 37° C., preferably approximately the same as the glass transition temperature Tg of the polymer material, which is typically about 50 to 65° C., and, in each case, below the melting temperature of the polymer material. The transition temperature may also be lower than the glass transition temperature Tg of the polymer material. Such a low temperature can only be used when there is enough time to carry out the operation and when the shape of the implant is suitable to be deformed by mainly mechanical means.

The shaping means 9 are provided with heating resistors, by which the pin 10 and the shaping surface 11 are heated.

FIG. 1a illustrates a step in which the tip part of the pin 10 of the tool is arranged in a hole 12 in the head of the implant. In this step, the pin 10 and the shaping surface 11 may already have been heated to a temperature required for heating the part of the implant 1 to an elevated temperature. Another alternative is to start heating the pin 10 in this step and possibly start heating the shaping surface 11 simultaneously.

The pin 10 is pushed P through the hole 12 deeper into the implant 1 material; the pin 10 may simultaneously be rotated R or vibrated V to advance the protrusion. The pin 10 heats and pushes the material away towards the second end 6 of the implant and also to the side. The head of the implant prevents the implant 1 from sliding deeper into the mounting hole 7. The hole 12 forms a contact surface, via which the mechanical energy caused by the motion of the pin 10 is transmitted to the implant 1.

As the implant 1 is heated with the pin 10 inserted therein, the inner section, i.e. the second section, of the shank 8 is heated most. Instead, the outer section, i.e. the first section, of the shank 8 for its part does not really heat much, owing to the low heat transmission capability of the shank material. The first section forms an attachment surface, which is pressed and attached against the tissue.

As a result of pushing the tool, the shaping surface 11 is pressed against the implant head and shapes the head to adapt to its shape. In FIG. 1b, the outer surface of the head has been shaped similar to the shaping surface 11. Heating advances the shaping of the head. The lower surface of the head has been pressed against the plate 2.

The second end 6 of the implant has swelled partly due to the material pushed by the pin 10 thereto and partly as a result of molecule relaxation caused by a temperature rise of the implant material. It is to be noted that the swelling of the second end is emphasized in FIGS. 1b and 1c for the sake of clarity.

In the step shown in FIG. 1c, the tool 4 has been pulled away from the implant 1. The implant 1 essentially keeps the shape, to which the pin 10 and the shaping surface 11 forced it—except for insignificant viscoelastic recovery.

The shank 8 forms an attachment surface, by which the implant 1 is fastened to the bone 3. The pin 10 has forced the diameter of the shank 8 to grow, whereupon the shank 8 has been pressed into the mounting hole 7. The fastening is essentially based on mechanical forcing, which is advanced by heating the implant 1. In an embodiment of the invention, the implant 1 or at least a part thereof is made of oriented material, the orientation direction of which is parallel or at least substantially parallel to the longitudinal axis C of the implant. Relaxation of polymer molecules caused by a temperature rise thus increases the tendency of the shank 8 diameter to grow.

The heating of the implant takes place so quickly that only part of the implant 1 material is heated to an elevated temperature. The surface of the implant shank 8 that is against the bony tissue 3 is heated quite little, wherefore no damages are caused in the bony tissue 3 by the elevated temperature.

Fastening the implant is a quick procedure, because it is easy and quick to insert the implant 1 into the mounting hole 7 and because the deformation of the implant 1 is achieved by heating and a short, mechanical shaping of only a part of the implant 1 material.

The grip between the shank 8 and the mounting hole 7 provides a very high pull-out strength corresponding to a conventional fastening screw. The pull-out strength is increased by the swollen second end 6 of the implant. The mounting hole 7 may also be provided with an undercut, which means that a mounting hole 7 wall may be provided with a cavity, into which the implant shank 8 may expand and which further increases the pull-out strength.

FIGS. 2a to 2e are schematic views of implants according to the invention.

Figure 2A:
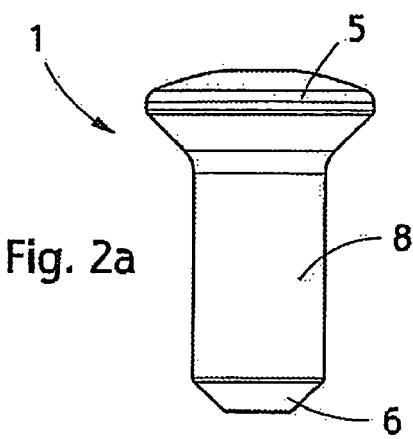
FIGS. 2a to 2f are schematic views of implants according to the invention.

The implant 1 of FIGS. 1a to 1c may be similar to that shown in FIG. 2a. The implant 1 comprises a substantially smooth-surfaced shank 8, i.e. its outer surface does not have shapes that increase the adhesion or pull-out strength of the shank 8. The first end 5 of the implant 1 comprises a head wider than the shank part 8, and the second end 6 is a bevel surface which facilitates the mounting. Such an implant provides the advantage of low manufacturing costs, for instance.

Figure 2B:
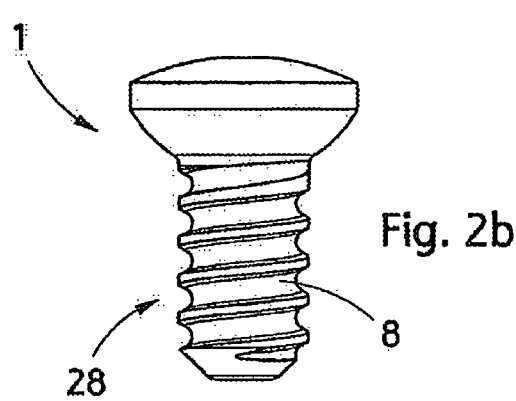

The implant 1 of FIG. 2b has a shape of a conventional fastening screw. Its shank 8 comprises one or more screw threads 28. The implant 1 may be mounted in the mounting hole by either driving it like a screw or simply inserting it into the mounting hole of suitable size in the tissue. The screw thread 28 may be threaded to an opening in the plate to be fastened. The implant model shown in FIG. 2b provides, for instance, the advantage that it reduces stress, such as thermal stress, applied to the tissue during the mounting. In addition, the screw thread 28 may strengthen the pull-out strength with respect to the implant shown in FIG. 2a.

Figure 2C:
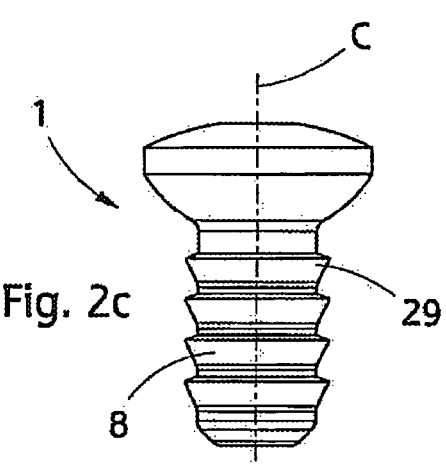

The implant 1 of FIG. 2c has a shape of a conventional fastening pin. The shank 8 of such an implant is provided with one or more, in this figure four, fastening edges 29 transversal to the central axis C of the implant. This implant model provides similar advantages to those of the implant shown in FIG. 2b.

Figure 2D:
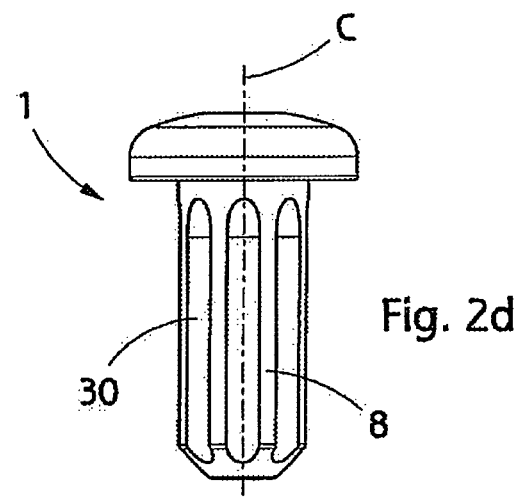

The implant 1 of FIG. 2d comprises a shank 8 with longitudinal grooves 30 parallel to the central axis C of the implant. The advantage of the implant model is, for instance, that the grooves lighten and reduce the mass of the implant. Furthermore, it is possible to integrate additional components in the grooves 30, or they may be utilized in, for instance, arranging a suture between the implant 1 and the mounting hole.

It may be noted that solutions according to the invention may also be used for fastening tendons, ligaments or tendon—ligament transplants to the bone, like interference screws in an ACL reconstructive operation or reconstructions or fastenings of tendons or ligaments of an ankle, foot, hand, wrist, shoulder or elbow. In this case, either a recess or a closed hole or a through hole is bored into the bone and both the implant and the tendon, ligament or transplant are mounted in this hole in parallel so that when the implant expands, it presses the tendon, ligament or transplant against the hole wall. The implants according to the invention may be used as suture anchors to fasten the suture to a bony tissue, for instance.

Figure 2E:
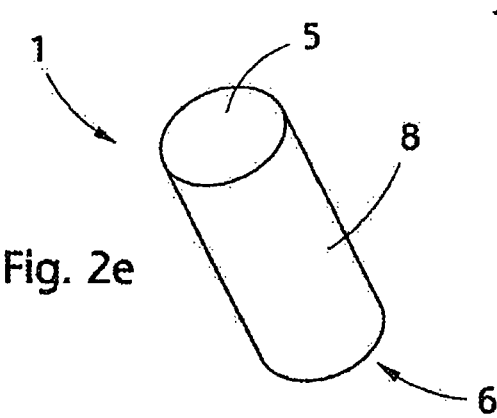

The implant 1 of FIG. 2e has a shape of a round cylinder. The implant 1 does not have a head that is wider than the shank part 8 nor any shapes that increase the pull-out strength. The first end 5 of the implant has a similar plane surface to that of the second end 6. This implant model provides the advantage, for example, that the manufacture is cost-efficient and that there are versatile ways of shaping it in situ. For example, the implant 1 may be cut from a longer bar to a suitable measure.

Figure 2F:
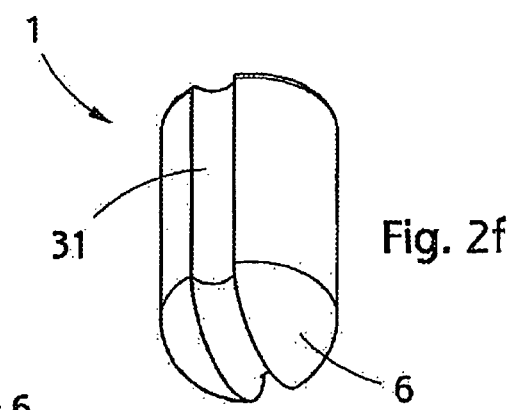

The implant of FIG. 2f comprises a surface groove 31, which extends around the shank 8 from the first side via the second end 6 to the second side. Such an implant 1 is particularly suited for fastening a tendon, ligament or transplant, for example. The shank 8 may naturally also comprise, for example, a thread 28, fastening edge 29 or longitudinal grooves 30. A suture fastened to the tendon, ligament or transplant end to be fastened to the bone may be arranged in the surface groove 31. After the implant 1 is mounted in its place in the mounting hole, the suture may be used for drawing the tendon, ligament or transplant to the bottom of the mounting hole and/or for keeping the tendon, ligament or transplant in its place before or while the implant 1 is finally mounted in the mounting hole.

The implant head or, more generally, the first end 5 of the implant comprises shapes, which enable the implant 1 to be fastened to the mounting tool and the rotating of the implant during the mounting. Such a shape may be a female shape, such as torx, hex socket or cruciform, or a male shape, such as hex head.

The implant 1 may be manufactured by manufacturing methods known per se, such as melt processing, i.e. injection moulding or extruding, drawing, machining from billets, compression moulding, or by using a plurality of methods known per se. If implant material is to be oriented, for instance drawing is employed. A drawn product, which is possibly cut into a suitable length, may be used as an implant according to FIG. 2e, for example. A drawn product may be a semi-finished product, from which the actual implant is manufactured by machining or compression moulding, for instance.

FIGS. 3a to 3f are schematic elevation views of implants according to the invention.

The implant preferably comprises a hole 12, which is concentric to the longitudinal axis of the implant and opens to the first end 5 of the implant. The depth of the hole 12 is only a fraction of the length of the implant, like in the implant 1 of FIGS. 1a to 1c, where the hole 12 is a recess having approximately the depth of the head part.

The hole 12 of the implant shown in FIG. 3a is a conical bottom hole tapering towards the second end 6 and extending close to the second end 6. At the mouth of the hole is a bevel 13, facilitating, for example, the mounting of the pin 10 in the hole 12. An advantage of such an implant is, for instance, that it may be heated safely by using a fiber laser taken into the hole 12. The conical hole 12 stabilizes the surface pressure of the tissue during deformation as a function of shank length, when a conical pin 10 is used for heating and shaping the implant. Accordingly, if a non-conical pin, such as a pin with a constant diameter substantially along the entire length or a pin the end of which comprises a spherical extension part, is used, the conical hole 12 causes the surface pressure against the tissue to increase towards the implant tip. In other words, the shank 8 of the implant tends to extend more at the second end 6 than at the first end 5.

The hole 12 of the implant shown in FIG. 3b is formed of two sections 32 and 33 with different diameters, connected to one another by a spherical surface 34. The hole 12 is a bottom hole as in the implant of FIG. 3a. An advantage of the implant is a small amount of head material, which speeds up the heating and shaping of the head. A hole 12 with a wide initial diameter may ease the pushing of the pin 10 into the shank 8.

The hole 12 of the implant shown in FIG. 3c is a conical through hole. A through hole provides the advantage that the pin 10 can be taken through the implant if there is space behind the implant. A guide may be arranged through the through hole, making it easier for an operator to arrange the implant in the right place with respect to the tissue. Furthermore, a suture thread fastened to the tendon, ligament or transplant end to be fastened to the bone may be threaded through the through hole in such a manner that by drawing the suture thread, said tendon, ligament or transplant may be pulled to the bottom of the mounting hole 7 provided in the bone, or the tendon, ligament or transplant may be kept in its place before or while the implant is finally fastened to the mounting hole 7.

The implant 1 of FIG. 3d comprises a through hole formed of an initial section 32 with a bigger diameter and an end section 33 with a smaller diameter, both sections having a cylindrical shape. The implant may be supported or pressed in the first section 32 by a suitable shaping part of the tool while the pin is inserted into the end section 33. The pin may simultaneously rotate or vibrate, thus heating the inner sections of the shank 8.

The hole 12 in the implant 1 shown in FIG. 3e is a through hole comprising three sections 32, 33 and 35 with different diameters. Between the sections there are conical surfaces 36. An advantage of such a hole 12 is that if the implant has enough space to expand, the second end 6 of the shank may be deformed more than the first end 5 or middle sections of the shank. Also, surface pressures of different magnitudes can be produced against the tissue at different points along the length of the shank 8. Here, the highest surface pressure can be produced at the second end 6 of the shank and the lowest surface pressure at the first end 5 of the shank. It is noted that the section of the hole having the smallest diameter need not necessarily be located at the second end 6 of the shank: it may also be located at the first end 5 or in the middle sections of the shank 8.

A difference in wall thicknesses may also be caused by changes in the diameter of the outer surface of the implant shank 8, the diameter of the hole being constant, or by a combination of changes in the diameters of the outer surface and the hole.

FIG. 3f shows an implant 1 without a head and the hole 12 of which is a cylindrical through hole. Such an implant 1 has low manufacturing costs and it can be shaped very freely in situ, for instance the implant length may easily be cut to a desired length in a cutting situation. An implant without a head can be mounted entirely inside a bone, which is often necessary in ACL (Anterior Cruciate Ligament) operations, for instance.

Any of the hole shapes shown in FIGS. 3a to 3f may be combined with an implant shape shown in any of FIGS. 2a to 2f. The cross section of the hole 12 is typically round, but it may also be a polygon. Along at least some of its length, the hole 12 may have shapes, which enable the implant to be fastened to the mounting tool and the implant to be rotated.

EXAMPLE 1

An implant according to FIG. 2e made of an oriented polymer with a draw ratio 4 was heated at a steady temperature in an oven for different times and dimensional changes were examined as a function of time. The outer diameter of the implant was approximately 4 mm.

It was found that a significant radial swelling took from dozens of seconds to few minutes, which was too much for practical applications. It was also found that the swelling took place at physiologically too high a temperature (70 to 90° C.).

It was also detected that the heat-induced swelling of the implant arranged in a loose mounting hole in the bony tissue stops at the wall of a bore channel. The pull-out strength achieved with the implant was marginal, below 50 N, and the produced surface pressure against the bone was approximately 1 MPa.

In addition, both oriented and non-oriented implants were mounted by inserting the implant into a tightly-dimensioned mounting hole provided in the bone and heated above Tg or the orientation temperature. In this way, no significant difference between an oriented and non-oriented implant was achieved in the pull-out strength (pull-out from the bone).

EXAMPLE 2

An implant of FIG. 3f made of an oriented material was arranged in a tightly-dimensioned mounting hole provided in the bone. The implant was forced to expand sideward towards the bone by inserting a hot pin 10 wider than the diameter of the hole 12 into the hole 12 of the implant. The implant expanded in few seconds, which was, in terms of clinical use, very quickly. As a result of the heating, a temperature gradient was formed at the implant, i.e. the shank thereof, whereby the temperature of the inner section of the implant, i.e. the shank part closely surrounding the hole 12, was 100 to 150° C., whereas the temperature of the outer surface against the tissue remained below 48° C. In other words, the temperature of the inner section of the implant was above the Tg temperature and/or orientation temperature of the manufacturing material of the implant and the temperature of the outer surface was below the Tg temperature so that temperature-induced cell damages could be avoided.

In the pull-out test, values above 100 N were achieved, which approximately corresponds to the pull-out strength provided by a degradable, clinically used screw of the same size in a threaded bore hole and in the same material. Reference tests were made with a Sawbones model bone (Sawbones solid rigid polyurethane foam; Pacific Research Laboratories, Inc., Wash., USA) by varying its density and with a real bony tissue (pig jawbone).

Also in the case of a porous bone, whereby the screw does not necessarily always provide a sufficient pull-out strength, in other words, the pull-out strength being well under 50 N, the implant according to the invention made a considerable improvement. The pull-out strength of the implant according to the invention was 50 to 100 N.

EXAMPLE 3

A non-oriented implant of FIG. 3f was arranged in a bone in the manner described in Example 2. By mechanically shaping or forcing the implant, such an implant also provided completely sufficient pull-out strength values in pull-out tests.

Depending on the application, non-oriented material may also be considered to be used, but it is advantageous to minimize the amount of foreign matter in the body and to use an oriented, stronger polymer whenever there is no other obstacle to use it.

EXAMPLE 4

A pull-out test was carried out to determine the maximum pull-out force of tacks according to the invention. Gamma-sterilized cannulated tacks having a head as presented in FIGS. 3b and 3e, for example, and an outer structure as presented in FIG. 2a with a stem diameter of 1.5 mm or 2.0 mm were put into holes drilled in a Sawbones model bone. A heated tip 10 connected to commercial soldering equipment was pushed into the hole 12 of the tack for heating and deforming the tack.

Sawbone blocks with pcf values 20, 30 and 40 were used as a model bone in fixation strength testing. Tacks were pulled out from the head with a constant speed of 5 mm/min. The maximum load was recorded in newtons (N).

Mechanical testing was performed either at room temperature (RT) or at 37° C. in a water bath. Prior to the testing, some of the foam-tack specimens were fully immersed in distilled water and conditioned at 37° C. either for 24 hours or for 1 week. Four parallel specimens were tested in each case. The average force values and the test conditions can be seen in the following Table 1.

TABLE 1

| | Tack diameter | | | | | | | |
|---|---|---|---|---|---|---|---|---|
| | 1.5 mm | | | | 2.0 mm | | | |
| | Foam | | | | | | | |
| | 20 pcf | 20 pcf | 30 pcf | 30 pcf | 30 pcf | 30 pcf | 40 pcf | 40 pcf |
| | Conditions | | | | | | | |
| | RT | 24 h/37° C. | RT | 24 h/37° C. | RT | 24 h/37° C. | RT | 1 week/37° C. |
| Pull-out force (N) | 73 | 55 | 82 | 72 | 140 | 105 | 150 | 74 |

The achieved results are sufficient or even excellent, being approximately the same or better than those of screws presently for sale.

FIGS. 4a and 4b are schematic elevation views of tools according to the invention.

The figures show shaping means 9 with a pin 10 and a concave shaping surface 11. In the solution of FIG. 4a, either the pin 10 or the shaping surface 11 or both may be heated. The pin 10 and the shaping surface 11 may have common heating means, with which they are heated simultaneously. Alternatively, the pin 10 and the shaping surface 11 may have their own separate heating means, whereby their temperatures may be adjusted independently of one another.

The heating element heating the pin 10 may be implemented in a variety of ways. One alternative is to use a wire-wound resistor, whereby a wire is wound around the body of the pin 10. It is also possible to use a thin-film resistor manufactured by, for example, vaporizing or a thick-film resistor manufactured by brushing or dipping, for instance. A tube resistor, which is manufactured by foaming, for example, may be used.

The shaping surface 11 may be heated by a resistance wire, for example. In the solution shown in FIG. 4a, the shaping surface 11 is in the shaping element 14, which is detachable from the tool 4 body. The shaping surface 11 to be heated may naturally be an integral part of said body.

The solution shown in FIG. 4b is otherwise similar to the solution of FIG. 4a, but here only the tip 15 of the pin, and not the whole pin 10, is arranged to be heated. Thus, the shank 16 of the pin is not heated. The tip 15 as well as the whole pin may be heated with similar solutions. Necessary conductors, contacts or the like are led to the tip 15 through the shank 16 of the pin.

The pin 10 part to be heated may not only be arranged at the tip 15 but also at a distance from the pin tip: there may be one, two or more such parts to be heated. Such a pin 10 to be partly heated provides the advantage that the heating can be accurately focused on a certain part of the implant, thus causing local deformations in the implant, which differ from the rest of the implant deformation.

FIGS. 5a to 5c are schematic elevation views of a second series of steps in the use of an implant and a tool according to the invention.

The implant 1 is used for fastening the plate 2 to the bone 3, which is provided with a mounting hole 7 for the implant.

The implant 1 of FIG. 5a is fastened to the tool 4 by arranging a fastening member 26 at the end of the tool 4 at a counterpart 27 in the head. The basic form of the counterpart 27 is a recess, but it may also be a protrusion, such as a hex head, in which case the fastening member 26 is a recess.

Between the fastening member 26 and the counterpart 27 there is an interference fit. The fastening member 26 and the counterpart 27 may be shaped in such a manner that rotational motion can be transmitted from the tool to the implant 1. This may be realized with, for example, a hex socket or torx driver or any other driver solution known per se.

The pin 10 is arranged to be movable so that it may be moved in its longitudinal direction with respect to the tool 4 body and the shaping means 9.

In FIG. 5a, the implant 1 is pushed P into the mounting hole 7. At the same time the implant 1 is rotated R and/or vibrated V. The rotating may take place in one rotation direction or, more preferably, in both rotation directions with a relatively small rotation angle. In addition to or instead of rotating, the implant 1 may be vibrated by means of vibratory motion parallel to its longitudinal axis. The frequency of vibratory motion is most preferably high, such as a few kilohertz, and the amplitude thereof is small, usually in the range of micrometers. The outer surface of the shank 8 now acts as both a contact surface and an attachment surface. The contact surface receives external mechanical energy either in the form of vibratory motion or rotational motion. The attachment surface attaches the implant 1 to the bone 3.

Between the implant 1 and the mounting hole 7 are contact points, which are formed of irregularities of either the mounting hole 7 or the implant shank 7 or both. At the contact points the outer surface of the implant 1 comes into contact with the wall of the mounting hole 7. Frictional motion between the implant 1 and the contact points make the surface parts of the implant, particularly the surface parts of its shank 8, heat starting from the contact points. The heating is restricted in such a manner that a temperature gradient is formed at the implant, the maximum of which is on the surface of the implant shank and wherein the temperature of the implant as a whole does not rise above the transition temperature of the first polymer material. The material of the shank surface does not melt, but the maximum value for the temperature is preferably above the first polymer material Tg, still more preferably above a possible orientation temperature. It is to be noted, however, that the maximum value of the temperature may also be lower than that of the first polymer material Tg.

In FIG. 5b, the implant 1 is inserted into the mounting hole 7 to its final mounting depth in the manner described above. The pin 10 is led to the bottom of the hole 12. As the pin 10 has proceeded in the hole 12, it has simultaneously forced implant material to move to the side and to press against the wall of the mounting hole 7. The pin 10 deforms and forces the implant against the bone 3 in such a manner that the implant fills in irregularities, hollows and cavities of the mounting hole 7 and the bone 3 and possibly packs the spongy bone surrounding the mounting hole 7. FIG. 5c shows the implant 1, which is detached from the tool 4 and fastens the plate 2 to the bone 3.

The pin 10 may be heated in such a manner that it heats the inner sections of the implant—yet so that the temperature gradient remains at the implant shank 8. The maximum of the temperature gradient may be either at the outer surface of the shank 8 or in the hole 12, and the minimum at some section of the shank 8 between the outer surface and the hole. The maximum value is preferably above the polymer material Tg and/or above a possible orientation temperature, but nevertheless below Tm.

The head part of the implant is shaped with the shaping surface 11, which may be heated. FIG. 5b illustrates how the shaping surface 11 is pressed against the head part of the implant, whereupon the head part is shaped according to the bevel of the mounting hole of the plate 2 and tightly fastens the plate to the bone 3.

EXAMPLE 5

Figure 10A:
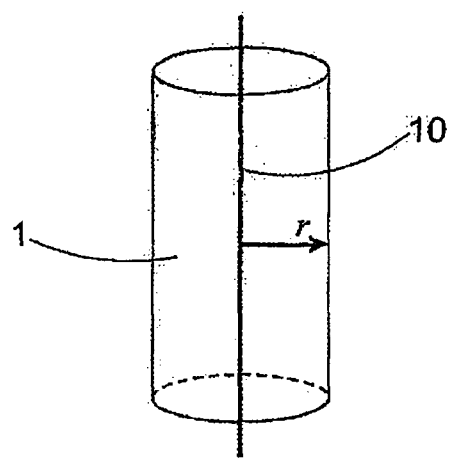
FIG. 10a is a schematic view of an implant and a tool according to the invention.
Figure 10B:
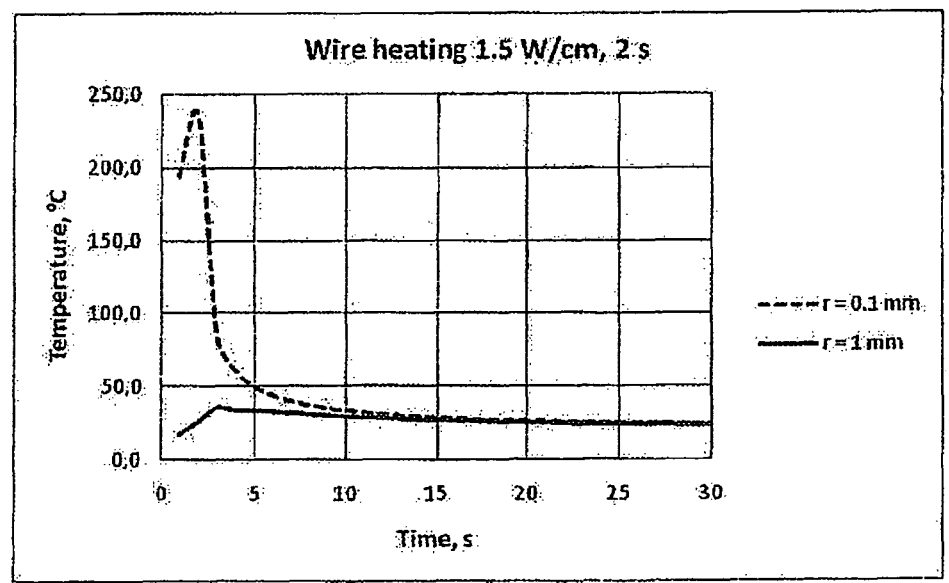
FIG. 10b is a graph of a temperature gradient of the implant shown in FIG. 10a, and FIG. 11 is a schematic view of still another indication of implants according to the invention.

FIG. 10a is a schematic view of an implant and a tool according to the invention, and FIG. 10b is a graph of a temperature gradient of the implant shown in FIG. 10a.

The implant 1 was heated from inside by means of a heated pin 10 for two seconds. The diameter of the implant 1 was 2 mm and the diameter of the pin 10 was 0.2 mm. FIG. 10b shows how the temperature changed in the inner section of the implant (r=0.1 mm) and in the surface of the implant (r=1 mm) during and immediately after the heating. The temperature in the inner section rose rapidly until the end of the heating, after which the temperature dropped quickly.

The maximum temperature value of the surface was achieved a little after the heating was ended. The figure shows that the surface temperature did not have time to rise considerably although the distance between the surface and the inner section and the heating pin was very small.

Figure 6C:
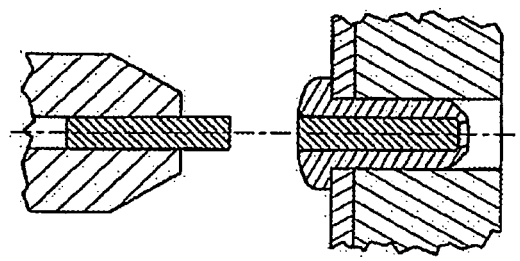
FIGS. 6a to 6c are schematic elevation views of a third series of steps in the use of an implant and a tool according to the invention.
Figure 6B:
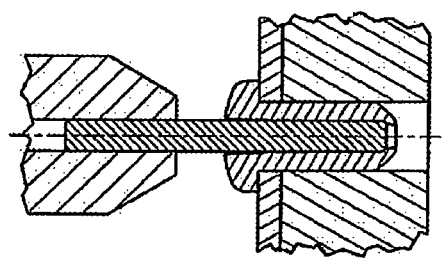
Figure 6A:
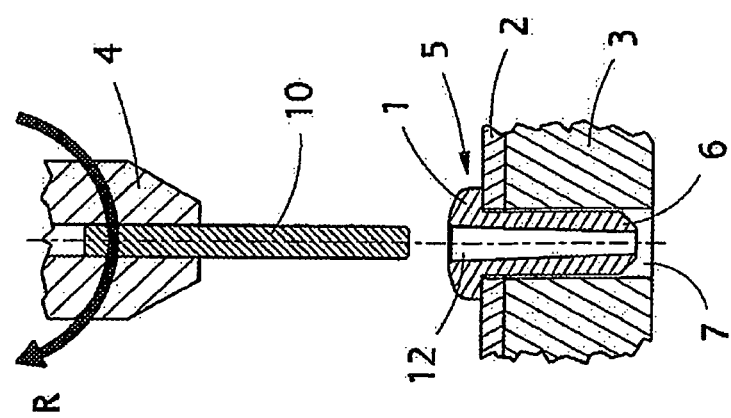

FIGS. 6a to 6c are schematic elevation views of a third series of steps in the use of an implant and a tool according to the invention.

FIG. 6a shows an implant 1, which fits loosely into the mounting hole 7. The mounting hole 7 is longer than the implant, extending through the bone 3. The implant comprises a conical through hole 12 tapering towards the second end 6 of the implant. The first end 5 of the implant further comprises a head that is wider than the shank part 8.

The tool 4 comprises a pin 10 arranged at the fastening means at the tool body. The pin 10 is made of a biocompatible material that may be left in the body. Such a material may include biodegradable or biostable plastic or metal or bioactive glass.

The diameter of the pin 10 is smaller than that of the hole 12 at the first end 5 of the implant. Instead, the diameter of the hole 12 at the second end 6 of the implant is smaller than the diameter of the pin 10. As the cross-sectional area of the hole 12 contracts, the pin 10 protruding forwards shapes the implant 1 mechanically.

The implant 1 may be heated by either heating the pin 10 or moving, such as rotating or vibrating, the pin 10 in the hole 12. To prevent the implant 1 from rotating or moving along with the pin 10 in the longitudinal direction, a separate instrument may be used or the tool 4 may be provided with fastening parts holding the implant in its place. Due to heating, the implant 1 may shorten in the hole, if it comprises oriented material.

Heating is by no means necessary in deforming the implant 1. The implant 1 may be shaped and forced against the surface of the mounting hole 7 by means of an unheated pin 10. An implant 1 deformed in such a way provides a pull-out strength that is sufficient in most applications of the implant.

If the pin 10 is made of an oriented polymer, it may expand while heated, which means that its diameter increases, which for its part may deform the implant 1.

After the implant 1 has been fastened to its place, the pin 10 is cut and the pin 10 part inside the implant 1 is left in the hole 12 of the implant 1. The pin 10 shown in FIGS. 6a to 6c is of a specific size, but it may also be continuous. A continuous pin 10 refers to a pin that is so long that other parts required for fastening a plurality of implants may be cut from it.

Figure 7A:
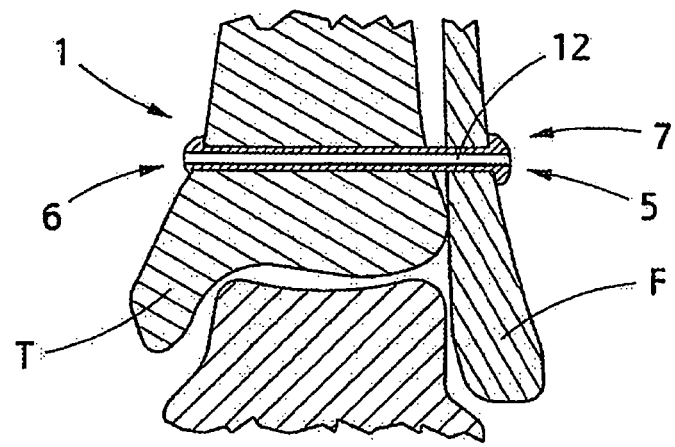
FIGS. 7a and 7b are schematic elevation views of indications of implants according to the invention.
Figure 7B:
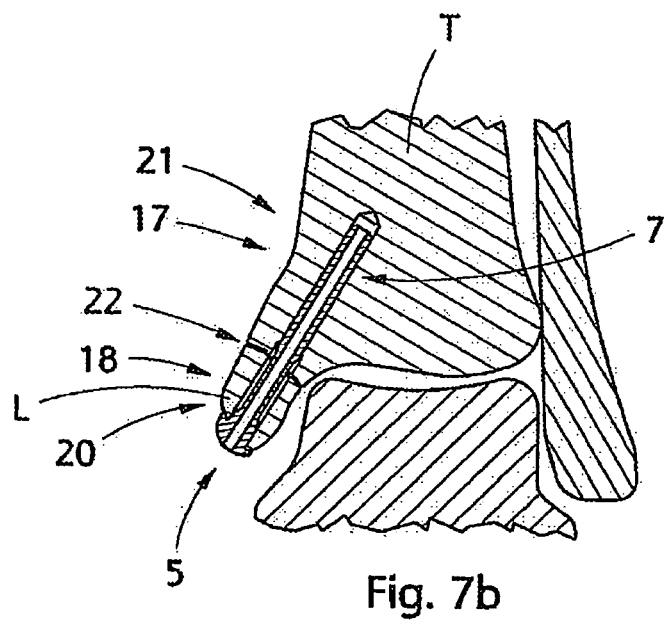

FIGS. 7a and 7b are schematic elevation views of indications of implants according to the invention.

FIG. 7a illustrates syndesmosis fixation, i.e. an operation in which a rupture of a syndesmosis ligament between the fibula and the tibia is fixed. The implant 1 is originally a round bar, the manufacturing material of which is most preferably oriented. The implant 1 is perforated by a longitudinal hole 12 with a constant diameter, and the first end 5 is provided with a head that is wider than the shank part. The implant 1 is inserted up to the head into the through holes bored through the bone.

The mounting hole 7 is formed of two sections provided in the fibula F and the tibia T. The implant 1 is taken via the mounting hole 7 from the side of the fibula through the fibula and the tibia in such a manner that the second end 6, i.e. distal end, of the implant 1 has passed through the tibia rear cortex and come out of the mounting hole 7.

The shank 8 of the implant is heated by the tool pin, whereupon the shank 8 has deformed and expanded against the walls of the mounting hole 7. Stress applied to the bones may be reduced and the mounting into the mounting hole 7 facilitated by making the diameter of the mounting hole 7 somewhat bigger than the diameter of the implant.

The second end 6 of the implant 1 is shaped by heating it with the tool pin 10 to an elevated temperature. As a result, the second end 6 has swollen and expanded, forming an expansion providing additional pull-out strength.

FIG. 7b illustrates an operation, in which a medial malleolar fracture of the tibia is fixed. A piece of bone L detached from the tibia T is fastened to the tibia by using the implant and method of the invention.

At the shank 8 of the implant there are a distal section 17, i.e. section closer to the second end 6, with a bigger diameter and a proximal section 18, i.e. section closer to the first end 5, with a smaller diameter. The initial section 20 of the mounting hole mainly provided in the piece of bone L has a bigger diameter than the end section 21 of the mounting hole provided in the tibia T. The initial section 20 thus extends over a rupture line 22 between the tibia T and the piece of bone L. The implant 1 is at first inserted into the mounting hole 7 so that the head at the first end 5 is settled against the piece of bone L.

The distal section 17 of the implant is arranged and fastened mainly inside the end section 21 of the mounting hole. The fastening has been carried out by heating and mechanically forcing the distal section 17 with the tool pin, which is not shown in the figure.

Instead, the proximal section 18 of the implant, which is entirely inside the initial section 20 of the mounting hole, is not fastened to the wall of said initial section. Consequently, the implant 1 has shut the rupture line 22 efficiently by drawing. If required, the head at the first end 5 of the implant 1 may be heated and mechanically forced to adapt better to the surface shape of the piece of bone L.

FIG. 8 is a schematic elevation view of a tool according to the invention.

The pin 10 comprises a hollow casing 23 with open ends and a photoconductive fiber 24 arranged therein. The fiber is connected to a light source for producing laser light, not shown in the figures. The pin tip is provided with a protection cap 25 transmissive to laser light and protecting the photoconductive fiber 24.

Laser light is led through the fiber 24 out of the pin tip to heat the implant 1 from inside. In FIG. 8, laser light heats the implant at the distal end of its hole 12. A laser beam is emitted directly out of the fiber parallel to the fiber 24 and the longitudinal axis C of the implant, hitting the bottom of the hole 12. The implant 1 is made either entirely or partly of a material absorbing the laser light wavelength used. Thus, the laser light energy absorbed in the material heats the material on the bottom of the hole 12.

After the bottom of the hole 12 has heated up suitably, the shaping surface 11 of the tool is pressed tightly against the head provided at the first end 5 of the implant, the head being adapted, as a result of the hot shaping surface 11 and mechanical forcing, to the shapes of the plate 2 to be fastened and the shaping surface 11. At the same time the pin 10 forces the part of the second end 6 of the implant at least mainly heated by laser to deform. In FIG. 8 the second end has already swollen a little. As a result, the second end 6 of the implant swells further and is pressed against the wall of the mounting hole 7 and partly expanded behind the bony tissue 3.

It is to be noted that the end of the fiber 24 may also be shaped in such a manner that laser light is directed at least partly to the side from it, i.e. away from the implant's centre line C. Such a fiber 24 or the whole pin 10 may be arranged to rotate about its longitudinal axis, which allows the implant material on the side of the fiber 24 to be heated. Heating may be arranged to take place along the entire length of the hole 12 when the pin 10 is inserted into the hole 12 or only at selected points of the hole 12.

The wavelength of laser is selected on the basis of, for instance, absorption and material properties of the implant 1, and it may be in the range of visible or IR light. Absorbent material, which is heated particularly easily by the effect of laser light, may be added to the implant 1 material; in this case, the rest of the implant material, such as the first polymer material, need not necessarily have the quality of receiving laser light energy—it may even be transparent to the laser light wavelength. The absorbent material may be distributed in the implant material either homogenically throughout the entire material volume of the implant or by forming local absorbent material concentrations in the material volume. The absorbent material may include, for example, insulator particles coated with a thin golden layer.

In this context, SPR (surface plasmon resonance) may be applied and the absorption of particles may be adjusted to a desired wavelength, such as the IR range. In practice, the adjustment is performed by taking into account the absorption when, for instance, the coating material or coating thickness is selected.

The implant 1 may also be heated by microwaves or radio waves. The implant 1 may comprise a polar component, such as N-methylpyrrolidone (NMP), absorbing microwave radiation (near field applicator). The implant heated in this way is deformed in the above manners.

The implant 1 may comprise an electrically conductive component, which may remain in the body permanently and which is used directly for heating the implant. Such a component may be a magnesium wire used as an electric resistance wire.

The implant 1 may comprise carbon, iron, barium titanate or other particles, which can be activated in an electromagnetic field (AC) by either its electric or magnetic component. The implant 1 may also comprise particles contributing to the absorption of focused ultrasound (HIFU) in the implant, affecting the reflection, refraction and scattering of ultrasound in the implant and thus the absorption of the focused ultrasound and heating of the implant.

The tool tip 10 may also be made of a material heating up to a constant temperature in the magnetic field (thermal seeds) or it may be a commercial component of PTC (positive temperature coefficient) type.

FIG. 9 is a schematic view of an operational principle of a tool and an implant according to the invention.

As was already stated earlier in this specification, the tool pin 10 may be wedge-shaped. This provides a wedge effect, by which force F pushing the pin 10 forwards is able to be converted into force $F_R$ directed to the side and forcing implant material to the side against the tissue and in most cases also into the tissue. For instance, if the diameter of the pin tip 37 is 0.4 mm and the diameter of the pin head 38 is 0.8 mm, the wedge angle $\alpha$ is 2.86° and the cone angle $2\times\alpha=5.72°$. Thus, the force directed to the side is $F_R=F/\tan 5.72=10F$. In other words, the force directed to the side is tenfold compared to the force F pushing the pin forwards. Consequently, a very good penetrability into a tissue, such as a bone, as well as an optimal pull-out strength of the implant are achieved by utilizing the combined effect of material relaxation and the wedge effect of the pin 10.

Figure 11:
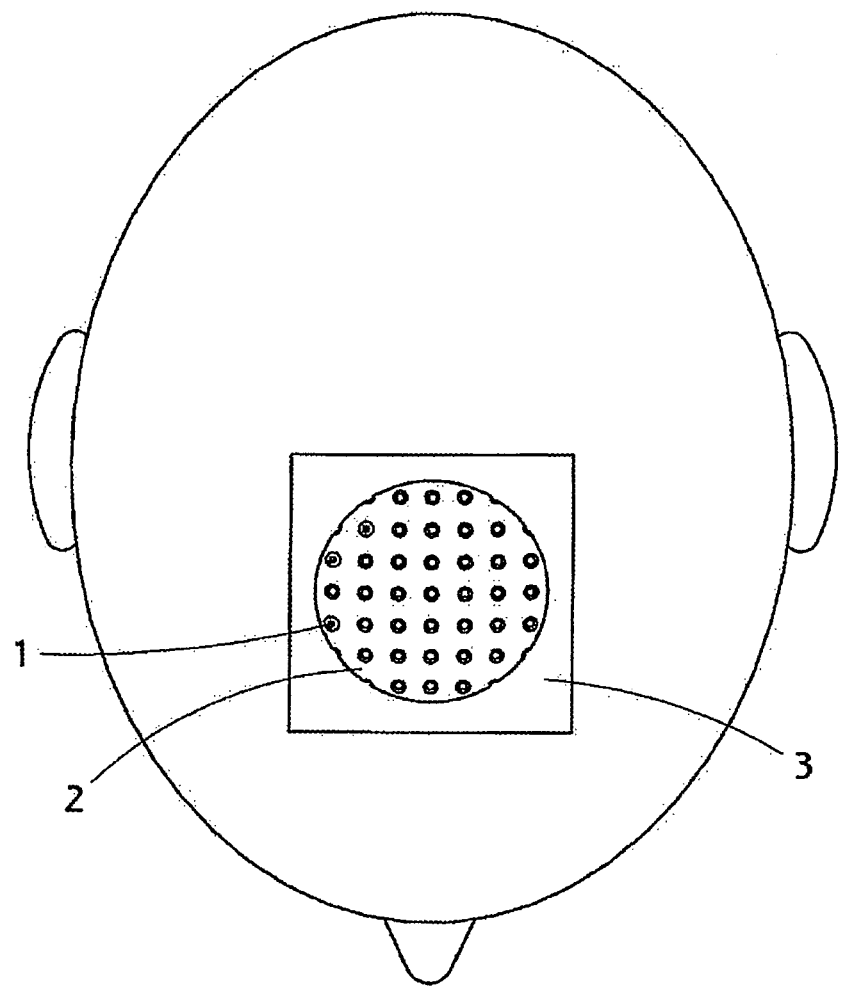

FIG. 11 is a schematic view of still another indication of implants according to the invention.

Here, the solutions according to the invention are used in a CMF-surgical (Craniomaxillofacial) application. The plate 2 is fastened to a skull bone 3 by implants 1. It is noted that the solutions of the invention may also be used for fastening tendons, ligaments or tendon-ligament transplants to the bone, like interference screws in an ACL reconstructive operations or reconstructions or fastenings of tendons or ligaments of an ankle, foot, hand, wrist, shoulder or elbow. In such cases, a fastening point is made to the bone by, for instance, drilling either a recess or a closed hole or a through hole. The implant and the tendon, ligament or transplant to be fastened is arranged at the fastening point in parallel so that when the implant expands, it presses the tendon, ligament or transplant against the wall of the fastening point of the bore channel.

The solutions of the invention may also be used in ossification operations of facet joints of the spine. In such an operation the implant is mounted in a slot provided through the zygapophyseal articulation in such a manner that the implant, when expanding, locks the articulation—and possibly draws the opposing surfaces of the intra-articular space together—thus enabling the articulation to ossify.

It will be obvious to a person skilled in the art that, as the technology advances, the inventive concept can be implemented in various ways. The invention and its embodiments are not limited to the examples described above but may vary within the scope of the claims.

The invention claimed is:

1. An implant to be fastened within a mounting hole in bone, the implant having a first end, a second end and an elongated shank made of a first polymer material,
    wherein the implant comprises a longitudinally aligned hole extending from the first end towards the second end, the longitudinally aligned hole constituting a contact surface for an implantation tool,
    wherein the elongated shank comprises an inner section of the first polymer material and an outer section of the first polymer material integrated with the inner section, the inner section of the elongated shank being configured to be heated to a higher temperature above a Tg temperature of the first polymer material to 100-150° C. but below the melting temperature of the first polymer material, and simultaneously, the temperature of the outer section being configured to remain at a lower temperature and below the Tg temperature of the first polymer material at about 48° C. to avoid temperature induced cell damage, such that the shape of the implant is deformable and lockable in the bone by the effect of forced mechanical expansion,
    wherein the first polymer material being oriented by a draw ratio of about 4, the main orientation direction being at least parallel to the longitudinal axis of the elongated shank; and wherein said outer section constitutes an attachment surface configured to expand the diameter of the elongated shank against the internal surface of said mounting hole in bone.

2. The implant as claimed in claim 1, wherein the outer section of the elongated shank is an attachment surface.

3. The implant as claimed in claim 1, wherein the longitudinally aligned hole has a surface tapering towards the second end of the implant.

4. The implant as claimed in claim 1, wherein the surface of the longitudinally aligned hole comprises said contact surface for receiving external mechanical energy.

5. The implant as claimed in claim 1, wherein the contact surface for receiving external mechanical energy is arranged at the first end of the implant.

6. The implant as claimed in claim 1, wherein the implant is made of a polymer blend comprising the first polymer material and at least one additional polymer material the melting temperature of which is higher than that of the first polymer material.

7. The implant as claimed in claim 1, wherein the first polymer material comprises additives and/or fillers which are arranged to intensify heating of the first polymer material.

8. The implant as claimed in claim 1, wherein an increased pull-out resistance of the implant from the mounting hole in the bone is achieved by utilizing a combined effect of a relaxation of oriented material and an increased forced mechanical expansion of the elongated shank sideward towards the internal surface of the mounting hole.

9. The implant as claimed in claim 8, wherein the increased pull-out resistance is from 50N to 100N.

10. A method for fastening a material within a mounting hole in bone, the method comprising steps of:
arranging an implant in the mounting hole in said bone, the implant having a first end, a second end, and an elongated shank being made of a first polymer material,
wherein at least part of the first polymer material being oriented by a draw ratio of about 4 prior to arranging the implant in the mounting hole in said bone, the main orientation direction being parallel to the longitudinal axis of the elongated shank,
wherein said oriented first polymer material constitutes an attachment surface configured to expand against the wall of said mounting hole in said bone, the implant further comprising a longitudinally aligned hole extending from the first end towards the second end,
wherein the elongated shank comprises an inner section of the first polymer material and an outer section of the first polymer material integrated with the inner section, the method further comprising steps of:
inserting a heated pin of an implantation tool wider than a diameter of the hole into the longitudinally aligned hole, the heated pin forcing mechanically the elongated shank to expand sideward towards the bone,
simultaneously heating the inner section of the first polymer material above a Tg temperature of the first polymer material to 100-150° C. but below the melting temperature of the first polymer material, and
simultaneously, keeping the temperature of the outer section of the elongated shank at a lower temperature and below the Tg temperature of the first polymer material, and
locking the implant deformed by the effect of mechanical energy in the mounting hole.

11. An implant to be fastened within a mounting hole in bone, the implant comprising:
a first end, an elongated shank and a second end,
wherein the implant includes a longitudinally aligned hole extending from the first end into the elongated shank towards the second end, with the elongated shank having a first outer section and a second inner section adjacent the longitudinally aligned hole, wherein the first outer section of the elongated shank is made of oriented polymer molecules oriented by a draw ratio of about 4 and including an orientation direction, wherein the orientation direction is parallel to the longitudinal axis of the elongated shank and the second inner section of the elongated shank includes relaxed polymer molecules,
wherein said oriented first polymer material constitutes an attachment surface configured to expand the diameter of the elongated shank against the internal surface of said mounting hole in bone.

12. The implant of claim 11 wherein the relaxed polymer molecules are formed by heating oriented first polymer material to a temperature above an orientation temperature for the first polymer material but below a melting temperature for the first polymer material.

13. The implant of claim 11 wherein the relaxed polymer molecules are formed by directly heating oriented first polymer material at the longitudinally aligned hole to a temperature above an orientation temperature for the first polymer material but below a melting temperature for the first polymer material.

14. An implant to be fastened within a mounting hole in bone, the implant having a first end, a second end and an elongated shank made of at least partly of a first polymer material,
wherein the implant comprises a longitudinally aligned hole extending from the first end towards the second end,
the longitudinally aligned hole constituting a contact surface for an implantation tool,
wherein the elongated shank comprises an inner section of the first polymer material and an outer section of the first polymer material integrated with the inner section, the inner section of the elongated shank being configured to be heated to a higher temperature above the Tg temperature of the first polymer to 100-150° C. but below the melting temperature of the first polymer material, and simultaneously, the temperature of the outer section being configured to remain at a lower temperature and below the Tg temperature of the first polymer material at about 48° C. to avoid temperature induced cell damage,
such that the shape of the implant is deformable and lockable in the bone by the effect of forced mechanical expansion, wherein at least part of the first polymer material being oriented by a draw ratio of about 4, the main orientation direction being parallel to the longitudinal axis of the elongated shank,
wherein the implant includes a longitudinally aligned hole extending from the first end towards the second end, the inner section surrounding said hole,
wherein said outer section constitutes an attachment surface configured to expand the diameter of the elongated shank against the internal surface of said mounting hole, and
simultaneously, the longitudinally aligned hole being configured to enlarge its diameter.

15. A method for fastening a material within a mounting hole in bone, the method comprising steps of:
arranging an implant in the mounting hole in said bone, the implant having a first end, a second end, an elongated shank being made of a first polymer material,
wherein at least part of the first polymer material being oriented by a draw ratio of about 4, the main orientation direction being parallel to the longitudinal axis of the shank,
wherein said oriented first polymer material constitutes an attachment surface configured to expand against the internal surface of said mounting hole, wherein the elongated shank comprises an inner section of the first polymer material and an outer section of the first polymer material integrated with the inner section, and wherein the implant includes a longitudinally aligned hole extending from the first end towards the second end, the inner section surrounding said hole, the method further comprising steps of:

inserting a heated pin of an implantation tool wider than a diameter of the hole into the longitudinally aligned hole, the heated pin forcing mechanically the elongated shank to expand sideward towards the internal surface of the mounting hole, simultaneously heating the inner section of the first polymer material above a Tg temperature of the first polymer material of the implant to 100-150° C. but below the melting temperature of the first polymer material, and simultaneously, keeping the temperature of the outer section of the elongated shank at a lower temperature and below the Tg temperature of the first polymer material at about 48° C. to avoid temperature induced cell damage, and expanding the diameter of the implant and locking it in the mounting hole by the effect of said mechanical energy, and simultaneously, expanding the diameter of the longitudinally aligned hole.

* * * * *